(12) United States Patent
Shibuya et al.

(10) Patent No.: US 8,153,130 B2
(45) Date of Patent: Apr. 10, 2012

(54) GRAFT-VERSUS-HOST DISEASE PREDICTING MARKER AND USE THEREOF

(75) Inventors: Akira Shibuya, Tsukuba (JP); Hiroshi Kojima, Tsukuba (JP)

(73) Assignee: University of Tsukuba, Tsukuba-shi (JP)

( * ) Notice: Subject to any disclaimer, the term of this patent is extended or adjusted under 35 U.S.C. 154(b) by 559 days.

(21) Appl. No.: 12/296,345

(22) PCT Filed: Apr. 5, 2007

(86) PCT No.: PCT/JP2007/057679
§ 371 (c)(1),
(2), (4) Date: Oct. 7, 2008

(87) PCT Pub. No.: WO2007/116945
PCT Pub. Date: Oct. 18, 2007

(65) Prior Publication Data
US 2009/0186017 A1    Jul. 23, 2009

(30) Foreign Application Priority Data

Apr. 7, 2006    (JP) ................................ 2006-106951

(51) Int. Cl.
*A61K 39/395* (2006.01)
(52) U.S. Cl. .................................. 424/145.1; 424/144.1
(58) Field of Classification Search ........................ None
See application file for complete search history.

(56) References Cited

U.S. PATENT DOCUMENTS

2005/0037969 A1    2/2005    Lu et al.
2007/0184444 A1    8/2007    Abbas et al.

FOREIGN PATENT DOCUMENTS

WO    2005016962 A2    2/2005

OTHER PUBLICATIONS

Toubai et al., Best Pract Res Clin Haematol. Jun. 2008;21(2):101-17.*
Nabekura et al., Proc Natl Acad Sci U S A. Oct. 26, 2010;107(43):18593-8.*
Webster's New World Dictionary, Third College Edition, 1988, see p. 1067-1068.*
Harlow et al., Antibodies, A Laboratory Manual, 1988, Cold Spring Harbor Laboratory, pp. 148-149.*
Acute GVHD, pp. 1-12, downloaded from "http://www.kfshrc.edu.sa/oncology/files/BMT%20Acute%20GVHD.pdf?bcsi-ac-87a1566f7576e15c=1D69644B000001022rVCTMpE39xPcNeHXvK/axFlksMIBAAAAgEAAPAiDwCEAwAABAAAAJkSBAA" on Sep. 1, 2011.*
James L.M. Ferrara et al., "Pathophysiology of Graft-Versus-Host Disease," Seminar in Hematology, 43: pp. 3-10, 2006, Elsevier.
Atsushi Kato, "III. Complication and Treatment of Hematopoietic Stem Cell Transplantation, 1. Graft-versus-host disease (GVHD)", Magazine from The Japanese Society of Internal Medicine, 94: 67-1343, 2005, English Abstract attached.
Yasushi Okoshi et al., "Analysis of CD226 expression on NKT cells of post allogeneic hematopoietic stem cell transplantation", The Japanese Society of Hematology, Aug. 30, 2005, 1 page, English translation attached.
Japanese Abstract, JP 2002-543825, pub. Dec. 24, 2002, entitled "Molecular Interactions in Hematopoietic Cells", inventors: Peter S. Lu et al., English language Abstract, equivalent to U.S. Patent Publication 2005/0037969.
Satoko Tahara-Hanaoka et al., Tumor rejection by the poliovirus receptor family ligands of the DNMA-1 (CD226) receptor), Blood, vol. 107, No. 4, Feb. 15, 2006, pp. 1491-1485.
Grazia Maria Spaggiari et al., "Mesenchymal stem cell-natural killer cell interactions: evidence that activated NK cells are capable of killing MSCs, whereas MSCs can inhibit IL-2-induced NK-cell proliferation", Blood, vol. 107, No. 4, Feb. 15, 2006, pp. 1484-1490.
Valerie Dardalhon et al., "CD226 is Specifically Expressed on the Surface of Th1 Cells and Regulates Their Expansion and Effector Functions", The Journal of Immunology, vol. 175, No. 3, 2005, pp. 1558-1565, The American Association of Immunologists, Inc.

* cited by examiner

*Primary Examiner* — Zachary Skelding
(74) *Attorney, Agent, or Firm* — The Webb Law Firm (57) ABSTRACT

A test method that provides data useful in predicting the probability of onset of acute graft-versus-host disease (GVHD) is described along with a kit for performing the method, and a pharmaceutical preparation and a molecular targeted therapy for treating or preventing GVHD. The test method includes measuring the blood DNAM-1 concentration of a patient of hematopoietic stem cell transplantation from bone marrow or the like over a period after the transplantation to provide data concerning the transition of the concentration to an abnormally high level deviating from the normal range, whereby the probability of the development of acute graft-versus-host disease is predicted, the risk of the development is estimated, or therapeutic effects after the development are evaluated. Concerning the molecular targeted therapy and pharmaceutical preparation used therefor wherein blood DNAM-1 of a GVHD patient or a graft recipient that is a possible patient is used as a target molecule, GVHD is treated or prevented by administering an anti-DNAM-1 antibody that is a neutralizing antibody.

6 Claims, 9 Drawing Sheets

GRAFT-VERSUS-HOST DISEASE PREDICTING MARKER AND USE THEREOF

FIELD OF THE INVENTION

The present invention relates to a method of assaying a DNAM-1 level associated with the onset of acute graft-versus-host disease as a graft-versus-host disease predicting marker, and relates to a kit therefor and a molecular targeted therapy using the method. In detail, the invention relates to a test method using a graft-versus-host disease predicting marker for providing data helpful in predicting or estimating the risk of acute graft-versus-host disease by determining the DNAM-1 level in a blood specimen, and relates to a kit therefor and a molecular targeted therapy using an anti-DNAM-1 antibody.

BACKGROUND ART

Blood plays a very important role in life-supporting by delivering oxygen to all parts of the body, or by attacking or protecting against nonself that has invaded the body. Blood contains three types of blood components: red blood cells, white blood cells and platelets. The white blood cells have a major and important function to protect a living body against nonself that has invaded the body, and they are classified into neutrophils, eosinophils, basophils, monocytes and lymphocytes. Accordingly, reduction in number of white blood cells disenables a living body to attack or eliminate pathogens that have entered the body, resulting in easy infection.

Leukemia is a disease in which white blood cells are malignantly transformed and proliferate mainly in bone marrow. Leukemia is subdivided into chronic leukemia and acute leukemia depending on the length of time in which it progresses when untreated, and each form is further divided into mygloid leukemia and lymphoblastic leukemia. Advanced leukemia destroys hematopoietic system and causes abnormalities such as reduction of normal white blood cells or platelets and anemia. And symptoms such as easy infection and bleeding tendency become clinically evident. When such hematopoietic dysfunction becomes worse, maintaining life will be threatened. Thus, leukemia is a fatal disease if untreated. Malignant lymphoma is a disease in which neoplastic lymphocytes proliferate mainly in lymph nodes, and is divided into Hodgkin lymphoma and non-Hodgkin lymphoma. Prognoses are varied depending on the lymphoma form, and a non-negligible number of cases result in death.

Hematopoietic tumors such as leukemia and malignant lymphoma have been addressed by killing tumor cells or normalizing the bone marrow function. Hematopoietic stem cell transplantation is one of such treatments. Each hematopoietic stem cell possesses capability to produce mature blood cells such as red blood cells and white blood cells, in other words, hematopoietic stem cells are multilineage potential, and they also have the potential to self-renew. Thus, they are mother cells for all the hematopoietic cells. Normal hematopoietic function may be recovered by eradicating tumor cells such as leukemia cells and malignant lymphoma cells by intense regimen of chemotherapy and radiation therapy and thereafter by transplanting hematopoietic stem cells.

Graft-versus-host disease that occurs after blood transfusion or stem cell transplantation is a serious side effect that should be addressed. Of the hematopoietic stem cell transplantations, allogeneic hematopoietic stem cell transplantation is often complicated with acute graft-versus-host disease (referred to as GVHD hereinafter) as an early complication.

Acute GVHD has a mechanism wherein activated T cells present in a graft from a donor recognize human leukocyte antigens (HLA) that express on the surface of white blood cells of a recipient (patient) as foreign and thereby the cytotoxic donor T cells attack cells of the recipient as foreign (Non-Patent Document 1). Patients having acute GVHD develop fever, skin rashes on limbs, face and trunk, liver damages with increased bilirubin, and digestive symptoms such as stomachache and diarrhea. GVHD is generally diagnosed by pathological examination on biopsy specimens of skin, liver and large intestine, but pathological findings are frequently not typical. Further, obtaining pathological materials is often difficult. Thus, there are many cases where this disease is diagnosed by clinical manifestations (Non-Patent Document 2).

A general choice for early treatment of acute GVHD is administration of steroids. Steroids are effective for acute GVHD but may cause serious side effects such as infection with bacteria and viruses, and therefore use thereof must be considered carefully. On the other hand, delay in starting the treatment of acute GVHD can invite a life-threatening result. Due to this dilemma, how to diagnose acute GVHD in clinical cases is a critical problem that influences the success of transplantation. At present, there are no methods capable of predicting the onset of graft-versus-host disease after bone marrow transplantation.

It is demanded that data should be provided which are useful as direct evidence in the diagnosis of acute GVHD. Clinical experts expect that an index is represented to allow for primary linking of a target identified acute GVHD with physiological and biochemical changes associated with immune responses, based on statistical significance. Further, there is a demand for data contributing to the prediction of probability of disease development and the estimation of risk of the development. However, no test methods for providing such data have been established for this disease. Thus, development of such test methods has been desired.

Needless to say, it is important that methods to effectively prevent or treat GVHD as well as the aforementioned test methods should be established and pharmaceutical preparations used for these methods should be developed.

Non-Patent Document 1: Ferranra J L, Redddy P., Pathophysiology of graft-versus-host disease, Seminar in Hematology, 43: 3-10, 2006

Non-Patent Document 2: Atsushi KATO, "Complications of hematopoietic stem cell transplantation and the treatment", 1. Graft-versus-host disease (GVHD)", Magazine from The Japanese Society of Internal Medicine, 94:67-1343, 2005

SUMMARY OF THE INVENTION

As described above, the diagnosis standards of acute GVHD are frequently dependent on surface symptoms such as fever and skin rashes on patients and have less objectivity. Further, current diagnosis methods do not have specificity for acute GVHD, and identifying the disease from other disorders is difficult. In view of the above circumstances, the present inventors studied the correlation between DNAM-1 found by an inventor of the present invention and acute GVHD in clinical specimens. It has been then found that DNAM-1 is involved in the mechanism of acute GVHD development. This finding has established the significance of DNAM-1 in blood as a predicting marker that is specific for acute GVHD. The present inventors thus accomplished the invention directed to acute GVHD-specific test methods capable of providing data useful in predicting the development of the disease, and kits for the methods, and the invention directed to GVHD molecular targeted therapy and pharmaceutical preparations for treating or preventing GVHD.

It is an object of the present invention to provide a test method and a kit therefor selectively used in the prediction of acute GVHD development, which method and kit give data for predicting the probability of acute GVHD development or estimating the risk of the development.

It is another object of the invention to provide a molecular targeted therapy and a pharmaceutical composition (preparation) used therefor wherein DNAM-1 in a GVHD patient or a recipient that is a possible patient is used as a target molecule and GVHD is treated or prevented by administering an anti-DNAM-1 antibody as a neutralizing antibody.

A test method for dealing with probability of GVHD development according to the present invention comprises determining the DNAM-1 concentration in blood collected from a transplant patient and examining temporal changes of the concentration to provide data for predicting the probability of development of acute graft-versus-host disease (GVHD) or for estimating the risk of the development.

The data may include classified blood DNAM-1 concentrations on the basis of a normal range that is within Mean+2 SD calculated from control values of healthy individuals, and a concentration exceeding this range is evaluated to be abnormally high.

The data may be preferably shown as a time-series profile of the blood DNAM-1 concentrations.

The time-series profile may be shown in sections and the sections contain time points at least two of which have a higher DNAM-1 concentration than that of an immediately previous time point and which do not show a decreasing change.

The transplant patient may be a bone marrow or peripheral, hematopoietic stem cell transplantation patient.

It is preferable that the data are mainly collected from a patient who has had allogeneic hematopoietic stem cell transplantation and are used to help prognosis management.

A test method of the invention provides a time-series profile showing blood DNAM-1 concentrations that is used for prognosis management for a patient who is under treatment of acute graft-versus-host disease (GVHD) or that is used for determination of therapeutic effects for GVHD.

The blood DNAM-1 concentration may be determined by ELISA method using a Tx25 monoclonal antibody.

A kit according to the present invention comprises at least a Tx25 monoclonal antibody, a human DNAM-1/Fc chimeric protein and an ELISA tool and is used to determine the blood DNAM-1 concentrations by performing an ELISA method using the Tx25 monoclonal antibody to create the time-series profile.

A pharmaceutical preparation for treating or preventing GVHD according to the present invention comprises an anti-DNAM-1 antibody or an analogue thereof that is a DNAM-1 neutralizing antibody. The anti-DNAM-1 antibody is preferably a monoclonal antibody.

Preferably, the anti-DNAM-1 antibody is a humanized DNAM-1 antibody that is expressed by a human DNAM-1 gene introduced in a DNAM-1 knockout mouse.

The pharmaceutical preparation for treating or preventing GVHD may further comprise at least a pharmaceutically acceptable excipient, carrier or stabilizing agent, and may further comprise a medicinal substance as an effective component for GVHD treatment.

The present invention also encompasses a use of an anti-DNAM-1 antibody in production of a pharmaceutical preparation for use in treating or preventing GVHD by administering the anti-DNAM-1 antibody or an analogue thereof that is a neutralizing antibody to blood DNAM-1 of a GVHD patient or a recipient that is a possible patient, as a target molecule.

In a molecular targeted therapy according to the present invention, blood DNAM-1 of a GVHD patient or a recipient that is a possible patient is used as a target molecule and GVHD is treated or prevented by administering an anti-DNAM-1 antibody or an analogue thereof that is a neutralizing antibody.

The test methods of the invention provide the most reliable data for predicting the probability of development of acute graft-versus-host disease (GVHD) or for estimating the risk of the development.

The data provided by the test methods of the invention are based on findings from immunopathology dealing with the probability of GVHD development, and are presented in an appropriate and convenient format.

With the data provided by the test methods of the invention, the probability of GVHD onset is predicted and early treatment of GVHD is possible. Therefore, a decrease in mortality from acute GVHD and improved accomplishments of bone marrow transplantation are expected.

The test methods of the invention are very useful in obtaining data for use in preliminary estimation of the risk of GVHD development, its early diagnosis, and prognosis management after hematopoietic stem cell transplantation from bone marrow or the like.

The pharmaceutical preparations for treating or preventing GVHD according to the invention comprise a neutralizing antibody specific for DNAM-1 involved in GVHD, and can effectively prevent or treat GVHD complication by being administered to hematopoietic stem cell transplantation patients.

In the specification, GVHD is defined as a disease in which lymphocytes and the like in a graft transplanted into a host of different histocompatibility antigen type, engraft in the host, and recognize host tissues as foreign and attack the tissues. In this case, the "host" is a recipient (transplant patient) who has received blood infusion or transplantation. The present invention is mainly targeted at a human and is suitably used for human patients. However, the invention may be used for non-human animals in which at least antibody formation by immune reactions is observed. The term "acute" is used herein as an antonym for "chronic".

The present invention will be described below in the order of test methods, kits for performing the methods, and DNAM-1 molecular targeted therapy for GVHD.

Test Methods

The test methods of the invention deal with a probability of development of acute graft-versus-host disease (GVHD).

In the methods, data for predicting the probability of development of acute graft-versus-host disease (GVHD) or for estimating the risk of the development are provided by determining the DNAM-1 concentration in blood and examining temporal changes of the concentration.

The test method includes measuring the blood DNAM-1 concentration in a specimen and statistically analyzing the data obtained. In the method, the specimen is serum prepared from blood. The blood is a blood specimen collected from a transplant patient who has received blood infusion or stem cell transplantation likely complicated with acute GVHD. In particular, the blood specimen is collected from a leukemia patient who has received bone marrow or peripheral, hematopoietic stem cell transplantation. Such patients are likely to develop acute GVHD after transplantation, and the risk of the development can be predicted. The blood may be collected from any parts of the body without limitation. The blood may be collected in an amount enough to ensure a required amount of serum for performing the ELISA method as described later, and the blood amount may be preferably 1 to 2 ml. The timing and number of blood collection may be referred to doctors for decision, but the blood may be preferably collected on a plurality of days in view of the purpose of the test.

Correlation Between DNAM-1 Molecule and Acute GVHD

DNAM-1 is a membrane protein discovered by Shibuya who is an inventor of the present invention (Shibuya A, et al., Immunity, 1996). DNAM-1 (CD226) is strongly expressed on activated T cells and NK cells having a cytotoxicity; they recognize ligands expressed on human tumor cells or the like and adhere thereto, playing an important role in inducing cytotoxicity against target tumor cells (Non-Patent Document 2). Part of the DNAM-1 molecules that have become more strongly expressed on the activated T cells are liberated from cell membranes and are released as soluble DNAM-1 in the blood stream. Therefore, the soluble DNAM-1 molecules that increase in blood of a recipient originate from white blood cells of a donor.

When T cells attack foreign cells or tumor cells, they adhere to the target cells and are activated, which initiates acute GVHD. In this process, cell adhesion molecules become involved as essential signal transducing molecules. Known adhesion molecules include cadherin family members bonding identical cells, integrin family members mainly expressed on white blood cells and involved in the bonding between cells or between a cell and an extracellular matrix, immunoglobulin family members playing roles in the bonding of cells, selectin family members and sialomucin family members involved in cell migration, and link family members involved in the bonding with an extracellular matrix. DNAM-1 is an adhesion molecule belonging to the immunoglobulin family. The present inventors advocate that this adhesion molecule when strongly expressed on activated T cells is involved in some way in the mechanism of acute GVHD development. In detail, DNAM-1 is involved in the bonding wherein donor T cells in a graft perceive recipient's white blood cells as nonself and are bonded thereto, with DNAM-1 recognizing a ligand expressed on the target cells and adhering thereto. In this process, DNAM-1 transduces an activation signal and induces cytotoxicity of the T cells.

An increasing number of researches supporting the above advocating have been accumulated. One of such researches presents comparison results between allogeneic transplantation and autologous transplantation as described later. In this connection, it is of particular interest that in 1991, Blazar et al. reported the involvement of an adhesion molecule lymphocyte function-associated antigen 1 (LFA-1) in acute GVHD. The present inventors have found that: through the innate behavior of NK cells or upon activation of T cells by recognizing antigens, DNAM-1 is associated with adhesion molecule LFA-1; a signal from LFA-1 induces tyrosine phosphorylation of DNAM-1 and consequently cytotoxicity is provoked; and DNAM-1 and LEA-1 are closely involved in the disease both functionally and physically (Shibuya A, et al., Immunity, 1999).

Soluble DNAM-1 Level in Blood and Temporal Changes Thereof

As described above, monitoring the expression and dynamics of DNAM-1 molecules which are found to be involved in acute GVHD is useful in diagnosis of acute GVHD. However, it is difficult to examine the expression of DNAM-1 molecules through characterizing T cells as a measuring target. Fortunately, DNAM-1 molecules are present as soluble DNAM-1 in blood of healthy individuals, and it is advantageous to use it as a disease marker. Such test methods have a high possibility of practical use.

Researches by the present inventors have demonstrated that soluble DNAM-1 in blood contributes to objective and specific diagnosis of acute GVHD. In detail, as will be demonstrated in Examples later, an increase of the soluble DNAM-1 level in blood has been shown to be closely associated with the onset of acute GVHD. Acute GVHD patients had higher blood DNAM-1 concentrations than before the onset of the disease. The inventors also confirmed that the blood DNAM-1 concentration did not increase in other blood diseases except acute GVHD. This indicates that the soluble DNAM-1 level in blood specifically changes with developing acute GVHD, but the level stays within the normal range with other blood diseases.

Accordingly, DNAM-1 molecules in blood are to be a specific predicting marker for acute GVHD onset, and detecting an increasing tendency of the level or a sign thereof enables prediction of the disease development. Thus, following temporal changes of the soluble DNAM-1 level in blood is an advantageous prognosis management after hematopoietic stem cell transplantation from bone marrow or the like. Accordingly, it is preferable that the data provided by the test methods of the invention are mainly collected from a patient who has had allogeneic hematopoietic stem cell transplantation and are used to help prognosis management. This is because allogeneic hematopoietic stem cell transplantation in which stem cells are offered by a related donor (a parent or brother) has much higher probability of acute GVHD development than autologous hematopoietic stem cell transplantation, as will be described in Example 1 later. This fact is based on inherent characteristics of immune system that strictly identifies self from nonself by HLA types.

In the test methods of the invention, the blood DNAM-1 concentration may be determined by any methods without limitation. A method capable of high precision measurement even with a trace amount of a specimen is preferable. In general, an analytical method using an antibody, preferably a monoclonal antibody, specific for DNAM-1 molecules is desirable because of its high sensitivity. For this purpose, the established ELISA method frequently used in the determination of analytes is suitable. In a preferred embodiment, the blood DNAM-1 concentration is determined by an ELISA method using a highly specific Tx25 monoclonal antibody. Further, it is preferable to use a kit that is designed to allow for rapid measurement by an ELISA method and ready acquisition of test results.

The test method of the invention not only determines the blood DNAM-1 concentration but also contributes to diagnosis of the probability of GVHD development. If a blood specimen taken from a test subject shows a high DNAM-1 concentration above the normal range, the data may be corroborative evidence indicating that the subject has or might have GVHD. In addition, the method of the invention characteristically provides data for specifically predicting the probability of development of acute graft-versus-host disease (GVHD) or for estimating the risk of the development. The test results finally presented to a doctor are shown in an appropriate format for the doctor to predict onset of the disease.

Formats of Test Data

The test results may be shown in various formats. The data finally presented by the test method of the invention classify blood DNAM-1 concentrations through statistical analysis based on a normal range that is within Mean+2 SD calculated from control values of healthy individuals, and a concentration exceeding this range is evaluated to be abnormally high.

Herein, "Mean+2 SD" means mean value+2×standard deviation, and only less than 2.5% of normal values exceed this range. Thus, if a blood DNAM-1 concentration is within the range, the concentration will be considered normal. As described later, the normal concentration of soluble DNAM-1 is not more than 0.098 nM. If the concentration is outside this normal range, it may be recommended to examine how much the concentration deviates from it and to take precautions against an increased probability of acute GVHD or to suspect that the disease has already developed.

The higher the blood DNAM-1 concentration, in other words, the more the concentration deviates from the normal range, the higher the tendency that acute GVHD will be developed in the future. However, it is dangerous to draw the conclusion with this result alone. In view of differences among individuals and variations by physiological conditions, it is necessary to obtain a pattern in which the blood DNAM-1 concentration is tracked over a time period.

Thus, the data may be preferably shown as a time-series profile of the blood DNAM-1 concentrations to allow for more objective diagnosis. Accordingly, the blood DNAM-1 concentration of a patient who has had hematopoietic stem cell transplantation from bone marrow or the like will be measured on days, namely, at a plurality of time points after the transplantation. From temporal changes of blood DNAM-1 concentration shown in the profile, the probability of acute GVHD development can be predicted. In other words, a sign of the disease onset can be predicted from a pattern of changes in blood DNAM-1 level. For example, if the blood DNAM-1 level shows a clear increasing tendency, it is reasonable to judge that the risk of the disease onset has increased. In a more preferred embodiment of the time-series profile to support the above judgment or estimation, the time-series profile is represented in sections and the sections contain time points at least two of which have a higher DNAM-1 concentration than that of an immediately previous time point and which do not show a decreasing change. According to this preferred embodiment, alarming points are clearly presented when a doctor examines GVHD probability using the data provided by the method of the invention.

In the time-series profile, the statistical analysis may be performed by methods appropriately selected from various statistical methods and test methods used in the art. Preferably, a statistical analysis method suited for analyzing temporal changes in discrete data is used, and the significance of the statistical results and the degree of risk are presented.

The data may be presented in a manner such that an index is presented which links acute GVHD development and blood DNAM-1 concentration based on statistics. As an example, the criterion concentration in blood as an upper limit of normal range may be 0.098 nM. This concentration is used as a parameter defined in the border with an abnormal range. By setting the cutoff level high as described above, a doctor can decide with high precision whether the condition is normal, the disease onset is potential and probable or is underway, or the disease has already occurred.

The data for predicting the probability of disease development or for estimating the risk of the development are beneficial because the temporal changes in blood DNAM-1 concentration give valuable clues. To increase the accuracy of the prediction or estimation, changes in other disease indexes may be used in combination with the above as required. For example, there are cases in which symptoms similar to the typical acute GVHD symptoms are observed due to frequent post-transplantation infection with various viruses, bacteria or fungi. To distinguish the target disease from such cases, the combined use as described above will be required. The presentation formats and manners for the test results are not limited to those described above, and various alterations and modifications are possible while still achieving the objects of the invention.

Predicting Probability of Disease Development and Estimation of Development Risk Predicting the probability of acute GVHD development or estimating the risk of the development is to estimate the likelihood, preferably stochastically, whether GVHD is not developed and no noticeable subjective symptoms are seen, or whether although the condition is almost healthy, immunologic, metabolic or physiologic changes leading to the disease are still potential, or whether such changes have progressed and the disease will be developed in the future. This probability prediction or risk estimation is very significant in preventive medicine, in particular from the aspects of prognosis prediction and follow-up. These deeds form an aspect of diagnosis. The term "diagnosis" is a medical act in which a doctor determines whether a patient is diseased or not based on symptoms and various test results, or determines the form, pattern and stage of the disease to treat the patient. The test methods of the present invention provide the most useful data for such diagnosis acts, i.e., for predicting the probability of disease development or for estimating the risk of the development. The data having the aforementioned embodiments and presentation manners are based on pathological findings on immune system that DNAM-1 in blood as a monitoring marker is specifically associated with acute GVHD development. The data are statistically supported, Therefore, the data can be used directly for the prediction of acute GVHD development.

The risk of the disease onset will be estimated in practice by a doctor in consideration of the data provided by the test method of the invention together with other clinical data and situations of an individual patient (age, gender, anamnestic history and lifestyle). The estimation based on such information becomes even more reliable.

If a patient is diagnosed to have a high possibility of future acute GVHD development, the patient is kept under prognosis observation so that the patient can immediately receive appropriate treatment upon the onset of the disease. In this manner, even if GVHD is developed, the patient can be treated early.

The data from the test methods of the invention are not only useful as a disease predicting marker specific for acute GVHD but also are significant in prognosis management after appropriate treatment of acute GVHD until remission. This is in a way retrospective from the standpoint of predicting and preventing acute GVHD development. In view of the finding that the blood DNAM-1 concentration characteristically changes such that it can be a disease predicting marker specific for acute GVHD, the data on the blood DNAM-1 concentration and changes thereof may be used as a monitoring marker that indicates pathological transition after treatment, or may be used as clinical data for evaluating therapeutic effects. Thus, the test methods of the invention include a test method that provides a time-series profile showing blood DNAM-1 concentrations that is used for prognosis management for a patient who is under treatment of acute graft-versus-host disease or that is used for determination of therapeutic effects.

Kits

The kit according to the present invention includes at least a Tx25 monoclonal antibody, a human DNAM-1/Fc chimeric protein and ELISA tools and is used to determine the blood DNAM-1 concentrations by performing an ELISA method using the Tx25 monoclonal antibody and create the time-series profile.

The kit contains various tools, materials and reagents required to perform the test method. Specifically, it contains the antibodies for the ELISA method, ELISA reagents, and reagents for determining the soluble DNAM-1 concentration in serum. The reagents include enzymes, standard substances for creating calibration curves, buffer solutions and washing solutions. The kit may also contain a set of required tools such as a microtiter plate for testing multiple specimens together. The specimen tested with the kit is preferably serum.

In a high-throughput embodiment of the test method according to the present invention, the kit may contain a microreactor tool, specifically a chip-shaped tool. In this constitution, a system is preferably adopted in which signals from the chip (semi) automatically analyzing the specimen are captured and finally transformed to be in the form of numerical values in an electronic file and the file is saved to a predetermined directory on a computer, whereby the numerical data are statistically processed to allow for estimation of the probability of disease development. For the data processing, the data may be subjected to required correction or normalization and then be processed using appropriate software capable of statistic analysis. The data processing system may be created by a skilled person using existing technology, methods and procedures.

DNAM-1 Neutralizing Antibody and Use Thereof in GVHD Treatment

The invention further provides GVHD treating or preventing pharmaceutical preparations (or pharmaceutical compositions) and GVHD molecular targeted therapy wherein an anti-DNAM-1 antibody or an analogue thereof is used as a DNAM-1 neutralizing antibody. The anti-DNAM-1 antibody that is an active component of the pharmaceutical preparations is preferably a monoclonal antibody.

Molecular Targeted Therapy for DNAM-1

Because the soluble DNAM-1 level is elevated when acute GVHD occurs, it can be safely said that the soluble or membrane DNAM-1 is involved in some way in acute GVHD. It was then assumed that DNAM-1 would be useful as a molecular target for prevention and treatment of acute GVHD. To develop methods and pharmaceutical compositions for treating or preventing GVHD, the present inventors studied molecular targeted therapy for DNAM-1 using murine GVHD models. In detail, they cloned DNAM-1 mouse homologous genes for the first time in the world (Tahara-Hanaoka, et al., Biochem Biophys Res Commun, 2005) to establish knockout mice, and prepared a neutralizing antibody for murine DNAM-1 (Tahara-Hanaoka, et al., Blood, 2006).

Researches using the neutralizing antibody for murine DNAM-1 demonstrated that: immunocytes involved with alloantigen specific immune response or inflammatory response related thereto are activated in acute GVHD to thereby excrete soluble DNAM-1; involvement of soluble or membrane DNAM-1 in some way in acute GVHD is strongly indicated; and acute GVHD can be prevented or treated by administering the anti-DNAM-1 antibody, as described in Example 4 later.

Of more than 20 clones of anti-DNAM-1 monoclonal antibody prepared by the present inventors, TX42 was the only neutralizing antibody. As this result indicates, preparing DNAM-1 neutralizing antibodies in acute GVHD is not easy. It should be also noted that the TX42 antibody destroys only the function of anti-DNAM-1 without reducing the number of DNAM-1 expressing cells by ADCC (antibody-dependent cell-mediated cytotoxicity) in vivo. Many of the antibodies induce ADCC to reduce the number of cells expressing the target molecule, resulting in frequent side effects such as weakened immune systems. In view of this too, the neutralizing antibodies such as the TX42 antibody having the above properties are advantageous anti-DNAM-1 antibodies for the prevention or treating methods of the present invention.

Based on this, an aspect of the present invention is directed to a molecular targeted therapy wherein DNAM-1 in blood of a GVHD patient or a recipient that Ls a possible patient is used as a target molecule and GVHD is treated or prevented by administering an anti-DNAM-1 antibody or an analogue thereof that is a neutralizing antibody. Here, the words "neutralizing antibody" refer to an antibody molecule that specifically binds to the target DNAM-1 molecule and has activity to suppress or destroy biological activity of DNAM-1 (in particular, physiological activity associated with GVHD development or pathological conditions) in vivo. It is assumed that in the presence of excessive DNAM-1, the neutralizing antibody specifically binds to DNAM-1 involved in the adhesion of donor T cells in a graft with white blood cells of a recipient and thereby interferes with the action of DNAM-1, so that the cell-mediated cytotoxicity is prevented from being induced to the T cells. By administering the anti-DNAM-1 antibody or an analogue thereof at a stage in which the blood DNAM-1 level starts to rise based on the test results, GVHD can be prevented or treated early.

Pharmaceutical Preparations for Treating or Preventing GVHD

The pharmaceutical preparations (or pharmaceutical compositions) for treating or preventing GVHD according to the present invention contain a DNAM-1 neutralizing antibody that is an anti-DNAM-1 antibody or an analogue thereof. For use as the anti-DNAM-1 antibodies, various types may be prepared by known techniques. When the pharmaceutical preparation is used for human, a preferred embodiment is as follows. The anti-DNAM-1 antibody is a humanized DNAM-1 antibody that is expressed by a human DNAM-1 gene introduced in a DNAM-1 knockout mouse as a human antibody-producing transgenic mouse. A chimeric antibody with a different animal species such as a mouse, rabbit or chicken may be used. The antibody that is immunoreactive preferably undergoes immune reaction specifically with DNAM-1, and may be a polyclonal antibody or a monoclonal antibody. In particular, monoclonal antibodies are preferable in view of properties such as antigen specificity, antigen affinity, neutralizing activity and cross reactivity. To prevent a side effect in which an antibody administered to a patient is recognized as a foreign protein and an immune response thereto is evoked, antibody humanization technology and techniques for producing humanized antibodies or monoclonal antibodies are used. Established and known methods may be used herein. For example, chimeric antibodies or humanized monoclonal antibodies may be prepared by techniques as described in Proc. Natl. Acad. Sci. USA (1983), 80, 7308-7312 by Teng, et al., and Immunology Today (1983), 4 (3), 72-79 by Kozbor, et al. Existing antibody producing cell lines such as CHO (Chinese hamster ovary) cells may be used for the production of antibodies.

The antibodies produced as described above may be subjected to appropriate modifications and alterations (fragmentation, complex formation with polypeptides or the like, modification for amino acid residues) as required while maintaining the ability as neutralizing antibodies. These variants obtained for the purpose of molecular stabilization, activity enhancement or controlling the half-life in blood are defined as analogues of the antibodies. These antibodies may also be used in the aforementioned test methods.

The pharmaceutical preparations of the invention may contain at least a pharmaceutically acceptable excipient, carrier or stabilizing agent, and may further contain a medicinal substance as an effective component for GVHD treatment. The medicinal substances include conventional medical agents for GVHD treatment such as steroids and immunosuppressive agents, and may further include substances capable of suppressing excessive expression of DNAM-1 genes. Pharmaceutically acceptable additives used may be, in addition to examples including substances conventionally used in the pharmaceutical industry, effectors such as macrophage-activating factors, substances enhancing stability or targeting ability of the anti-DNAM-1 antibody, and substances improving the half-life in blood of the antibody. The pharmaceutically acceptable carriers and excipients are known to the skilled person and include salts, sugars, other osmoregulators, buffering agents, acids, bases, other pH adjusters, viscosity improvers and colorants.

The forms of the preparations that are antibody drugs are not limited, and the preparations may be provided in the forms of freeze-dried preparations, powder preparations, solution preparations with pH-adjusted buffer solutions, and injectable microcapsule preparations. In the case of injectable preparations as an example, the antibody may be added together with required or desirable excipients and/or additives to a biocompatible or physiologically acceptable liquid carrier (preferably aqueous carrier) to give an injectable or infusible suspension or dispersion. These additional components may be added based on conventional formulating technology in the art. For example, they may be dissolved or suspended in a pharmaceutically acceptable nontoxic carrier such as saline or commercially available injectable distilled water such that the concentration will be 0.1 µg antibody/ml carrier to 10 mg antibody/ml carrier.

Another aspect of the present invention provides a use of an anti-DNAM-1 antibody in production of a pharmaceutical preparation for use in treating or preventing GVHD by administering the anti-DNAM-1 antibody or an analogue thereof that is a neutralizing antibody to blood DNAM-1 of a GVHD patient or a recipient that is a possible patient, as a target molecule.

Uses

The pharmaceutical preparation of the invention is administered to a patient in the form of an injectable preparation or an instillation preparation, specifically via intravascular administration or intravenous administration, in both cases of treating and preventing GVHD. Appropriate doses, concentrations, administration routes, timing and formulation may be individually determined by a doctor in consideration of symptoms and conditions of the patient in relation to the above GVHD treating or preventing methods. The doses may vary depending on patient conditions, administration purposes (whether it is for treatment or preventive) or types of the active components (e.g., the antibodies, the medicinal substances). For an adult, the preparation may be generally administered in the range of 10 µg to 1000 mg, and preferably 10 µg to 500 mg per administration. In the case of an injectable preparation, the preparation may be administered to a human patient one to several times in a day at a ratio of 1 µg to 100 mg, and preferably 50 µg to 50 mg per kg of the patient in each administration.

BRIEF DESCRIPTION OF THE DRAWINGS

FIGS. 6-1A and 6-1B illustrate respectively post-treatment changes in blood DNAM-1 concentration of two patients (YU and NK) who were transplanted with allogeneic bone marrow hematopoietic stem cells from unrelated donors and were complicated with acute GVHD, wherein "PSL" and "mPSL" mean methylprednisolone, "Alp" serum alkaline phosphatase, "Pulse" pulse treatment, and "MMF" mycophenolate mofetil, and wherein the negative values are as a result of data processing subtracting the blank in the ELISA method;

FIGS. 6-2 shows changes in blood DNAM-1 concentration of a patient (YM) transplanted with allogeneic hematopoietic stem cells from an unrelated donor, over phases before and during acute GVHD development and after treatment, wherein indications and symbols are the same as in FIG. 6-1;

BEST MODE FOR CARRYING OUT THE INVENTION

Examples

Material sources, numerical conditions such as reagent concentrations and amounts, treating time and treating temperature, and treating methods used in Examples are no more than preferred examples. Thus, it should not be construed that Examples limit the scope of the present invention.

Example 1

Correlation Between Blood Diseases and Soluble DNAM-1

The soluble DNAM-1 level in blood was measured to determine whether DNAM-1 was involved in the development of acute GVHD and whether or not DNAM-1 would increase at an initial onset of various blood diseases. To determine the soluble DNAM-1 concentration in serum, ELISA method was used.

Subjects and Specimens

Clinical specimens were collected from 39 individuals (18 GVHD-positive transplant patients and 21 GVHD-negative transplant patients). In detail, serum from patients who received hematopoietic stem cell transplantation at Tsukuba University Hospital since November, 2001 was preserved at −70° C. with the consent of the patients and was used as specimens in the test. Serum from a transplantation donor was used as a healthy control.

Reagents and Antibodies

Tx25 hybridoma is a cell developed by one of the inventors of the present invention. Tx25 hybridoma was inoculated in the peritoneal cavity of a BALB/cA-nu female mouse (6 weeks old), and the ascitic fluid was collected. Thereafter, Tx25 monoclonal antibody was isolated using MAb, Trap kit purchased from Amersham Bioscience (Uppsala, Sweden).

Recombinant human DNAM-1/Fc chimeric protein and biotinylated anti-human DNAM-1 polyclonal antibody were purchased from R&D System (Minneapolis, Minn.), and ExtrAvidin peroxidase (including a mouse ExtrAvidin peroxidase staining kit) and Fast o-phenylenediamine dihydrochloride (OPD) tablets were purchased from SIGMA-ALDRICH (Saint Louis, Mo.).

Buffer solutions used were PBS which contained 8000 mg NaCl, 200 mg KCl, 1150 mg $NaHPO_4$ and 200 mg $KH_2PO_4$ in 1000 ml, and T-PBS which was prepared by mixing 1000 ml of PBS with 500 μg of Tween 20®.

ELISA Method

The Tx25 antibody diluted with PBS to 8 μg/ml was applied to an ELISA 96 well (12×8) flat-bottom microplate (DYNEX TECHNOLOGIES, Chanitilly, Va.) at 100 μl/well and was immobilized at 4° C. overnight. The microplate was then washed with PBS three times each for 5 minutes, and blocking was performed with 1% BSA/PBS for 1 hour at room temperature. The microplate was washed with PBS two times each for 3 minutes. The wells in the first line were charged with 100 μl/well of the human DNAM-1/Fc chimeric protein standard in an eight-step dilution series from 2 nM prepared with PBS containing 0.05% Tween 20 (T-PBS). The wells in the second and later lines received 100 μl/well of patient serum. The microplate was left for 4 hours at room temperature and was washed with T-PBS three times each for 10 minutes. The wells were then applied with 100 μl/well of the biotinylated antihuman DNAM-1 antibody diluted with T-PBS to 0.6 μg/ml, and were left for 1 hour at room temperature. The microplate was washed with T-PBS three times each for 10 minutes. ExtrAvidin peroxidase diluted 250 times with T-PBS was added at 100 μl/well, and then the microplate was left for 30 minutes at room temperature and was washed with T-PBS three times each for 10 minutes. The peroxidase enzyme activity was measured at OD 405 nm using OPD as a chromogenic substrate.

Figure 1:
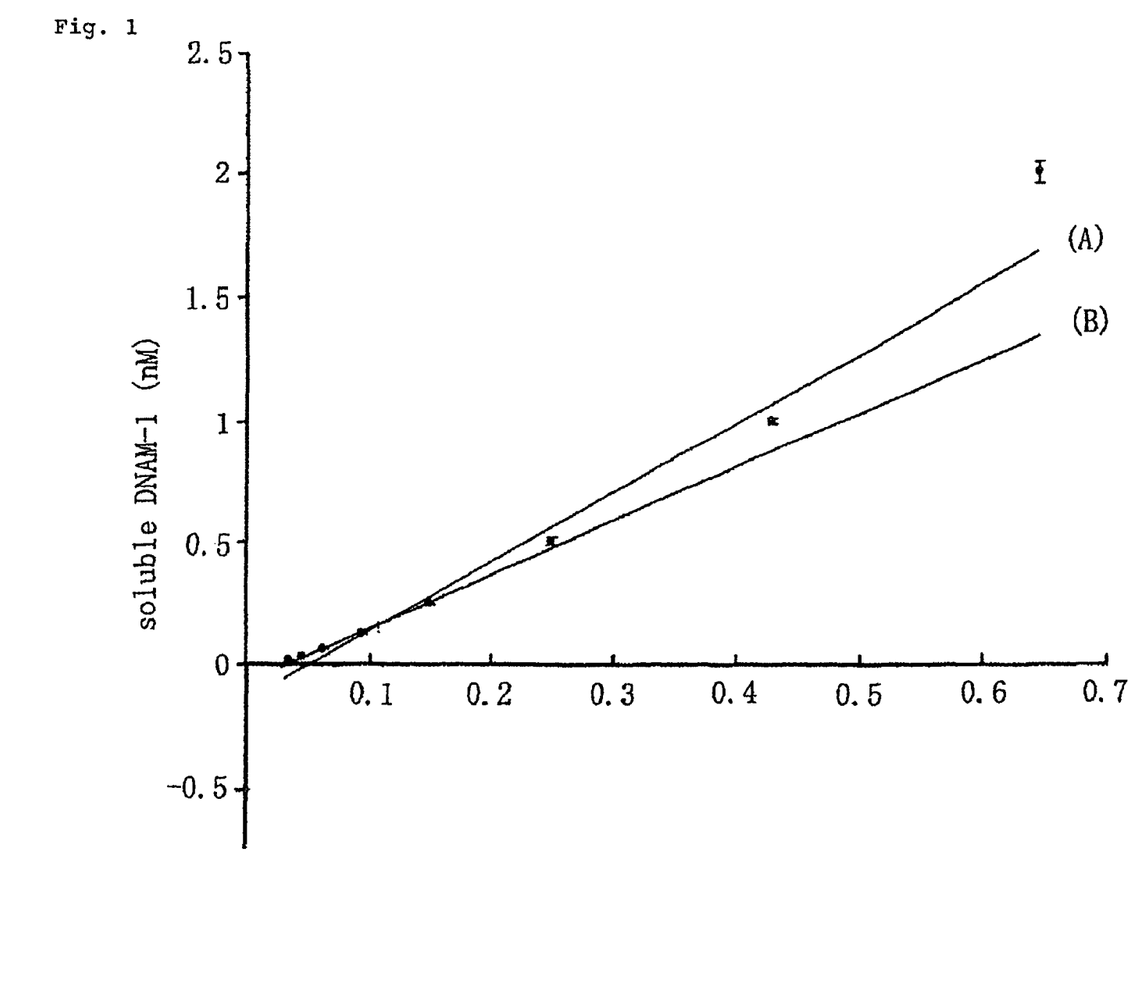
FIG. 1 indicates calibration curves for determination of DNAM-1 concentration by ELISA method wherein the calibration curve (A) is drawn on DNAM-1 concentrations ranging from 0.015625 nmol to 2 nmol and the calibration curve (B) is created based on DNAM-1 concentrations from 0.015625 nmol to 0.5 nmol, wherein the vertical axis shows soluble DNAM-1 concentration and the horizontal axis shows $OD_{405\ nm}$ value.

In the eight-step dilution series of DNAM-1, the data obtained at from 0.0156 nM to 0.5 nM, a range thought to reflect the practical soluble concentration in patient serum were used to create a calibration curve (FIG. 1). The soluble DNAM-1 concentrations in serum were determined based on the calibration curve.

Results for Various Blood Diseases

"Mean+2 SD (mean value+2×standard deviation)" was calculated from control values of healthy individuals and was defined as a normal range. When the concentration exceeded this ranger it was evaluated to be abnormally high. The normal concentration of soluble DNAM-1 was not more than 0.098 nM.

Figure 2:
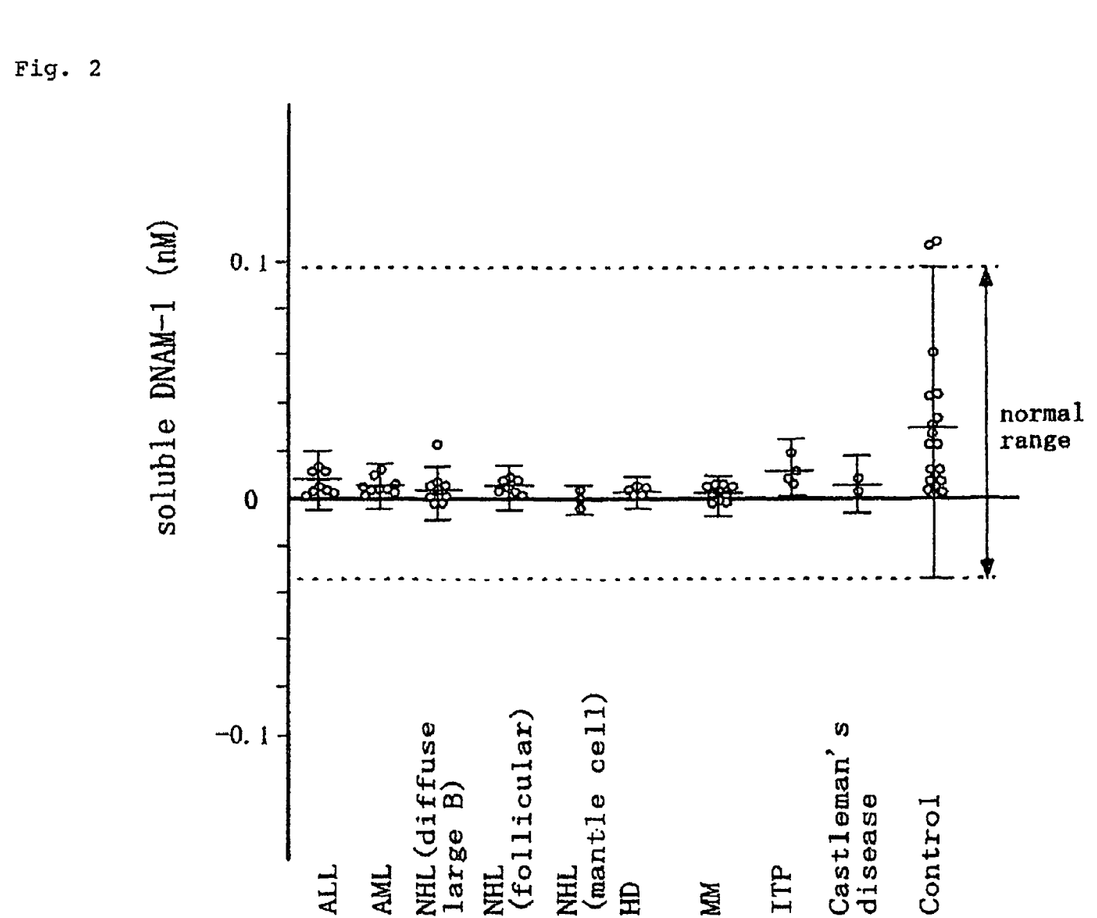
FIG. 2 shows soluble DNAM-1 concentrations in blood at an initial onset of various blood diseases described in the specification, wherein "Control" is a standard and provides a normal range.

As indicated in FIG. 2, although only one specimen had a concentration far out of the normal range in Castleman's disease, the soluble DNAM-1 concentrations in serum of all the patients were found in the normal range in ALL (acute lymphocytic leukemia), AML (acute myelogenous leukemia), NHL (non-Hodgkin lymphoma; "diffuse large B"; "follicular"; "mantle cell"), HD (Hodgkin disease), MM (multiple myeloma) and ITP (immune thrombocytopenic purpura).

Results for Acute GVHD

The soluble DNAM-1 concentration was measured after allogeneic transplantation possibly complicated with acute GVHD and autologous transplantation. In autologous transplantation, a patient is transplanted with frozen bone marrow or peripheral hematopoietic stem cells collected from himself and is not assumed to be complicated with acute GVHD.

Figure 3:
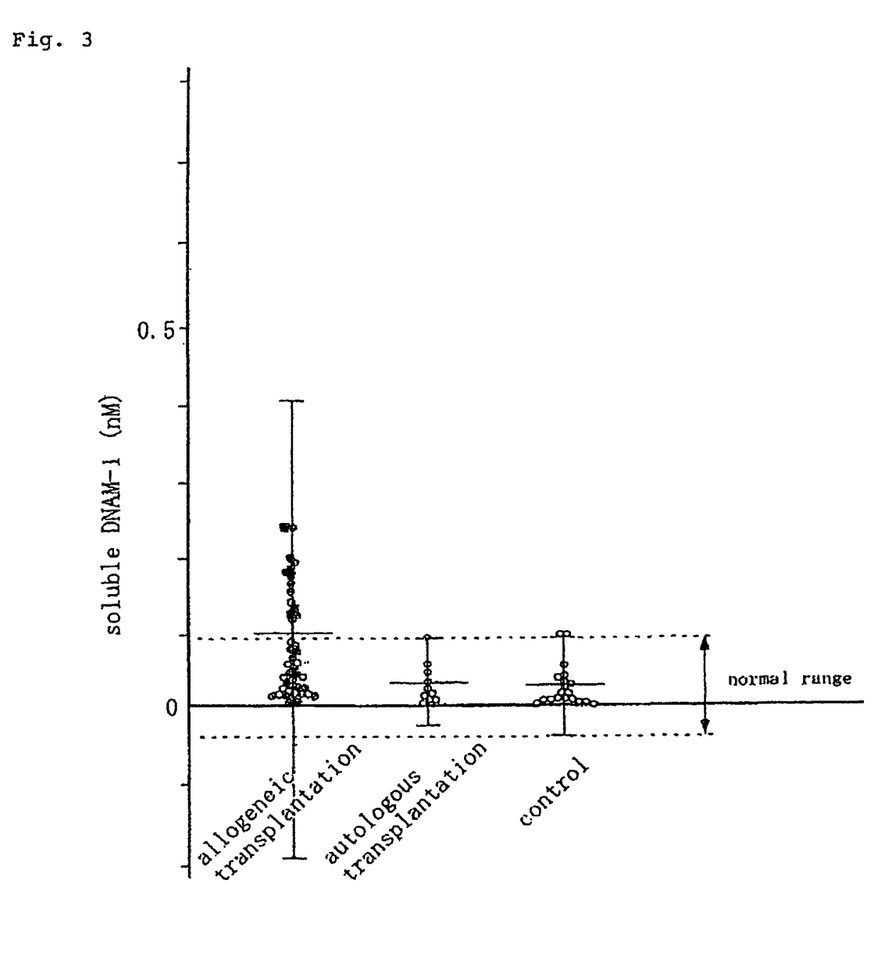
FIG. 3 shows soluble DNAM-1 concentrations in blood after allogeneic transplantation and autologous transplantation comparing peak values of subjects clinically diagnosed to have acute GVHD, indicated by "●" plot points, and of subjects clinically suspected to have acute GVHD, indicated by "■" plot points.

As a result, 90% of the serum specimens of the autologous transplantation patients were found within the normal range but 45.7% of the serum specimens of the allogeneic transplantation patients exceeded the normal range as indicated in FIG. 3.

The above results show that the soluble DNAM-1 concentration in blood does not increase at an initial onset in many of the blood diseases but does specifically increase in acute GVHD. This will indicate involvement of DNAM-1 in some way in the process in which donor T cells damage recipient cells. 85.7% of the allogeneic transplantation patients who showed a high level of soluble DNAM-1 had been complicated with acute GVHD.

Figure 4:
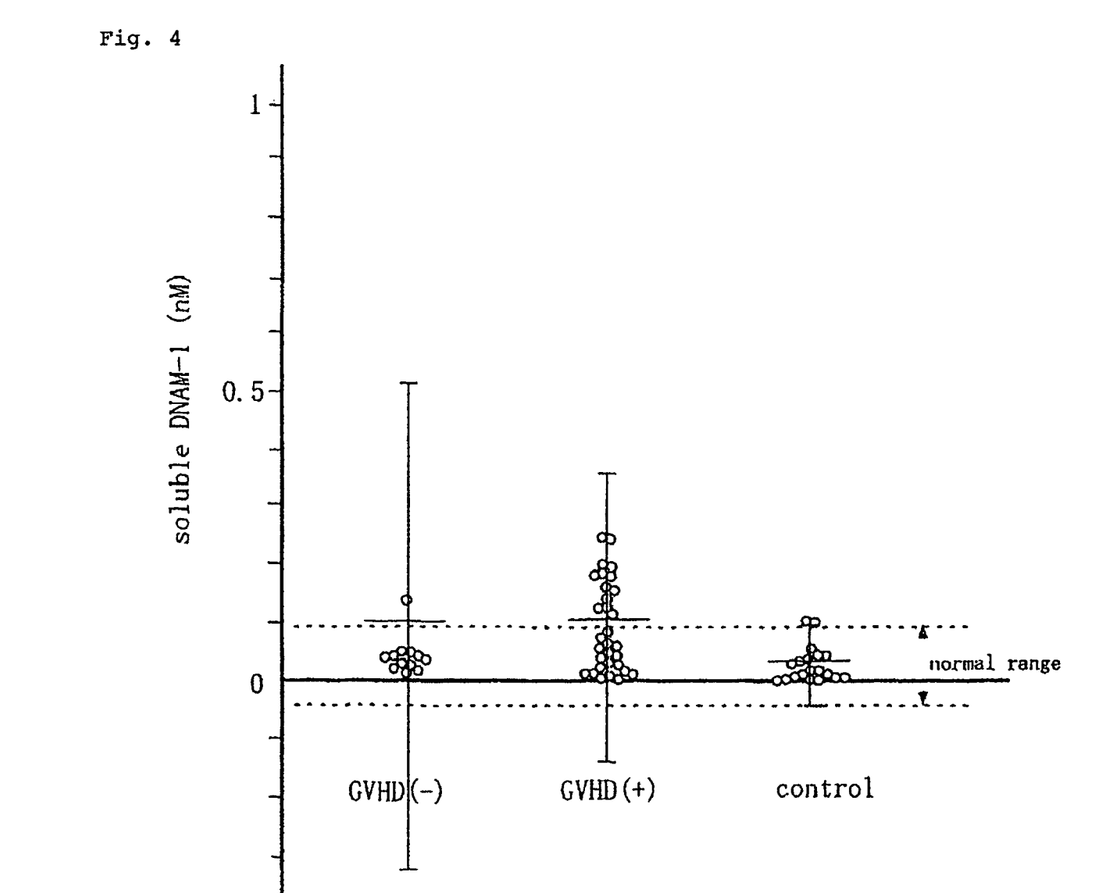
FIG. 4 shows a correlation between acute GVHD occurrence and soluble DNAM-1 concentration comparing peak values of soluble DNAM-1 concentration between acute GVHD positive and acute GVHD negative after allogeneic transplantation, wherein the upper and lower dotted lines are drawn at 0.0983 and −0.0375, respectively.

FIG. 4 compares the specimens of the allogeneic transplantation patients between acute GVHD positive and acute GVHD negative, As shown, 80% of the acute GVHD negative patients had a soluble DNAM-1 concentration in the normal range, whereas 58.1% of the acute GVHD positive patients had a concentration exceeding the normal range.

Thus, it can be safely said that when the soluble DNAM-1 concentration in blood exceeds the normal range, acute GVHD has developed, will soon develop, or can possibly develop.

Example 2

Examples of Data Presentation

Figure 5:
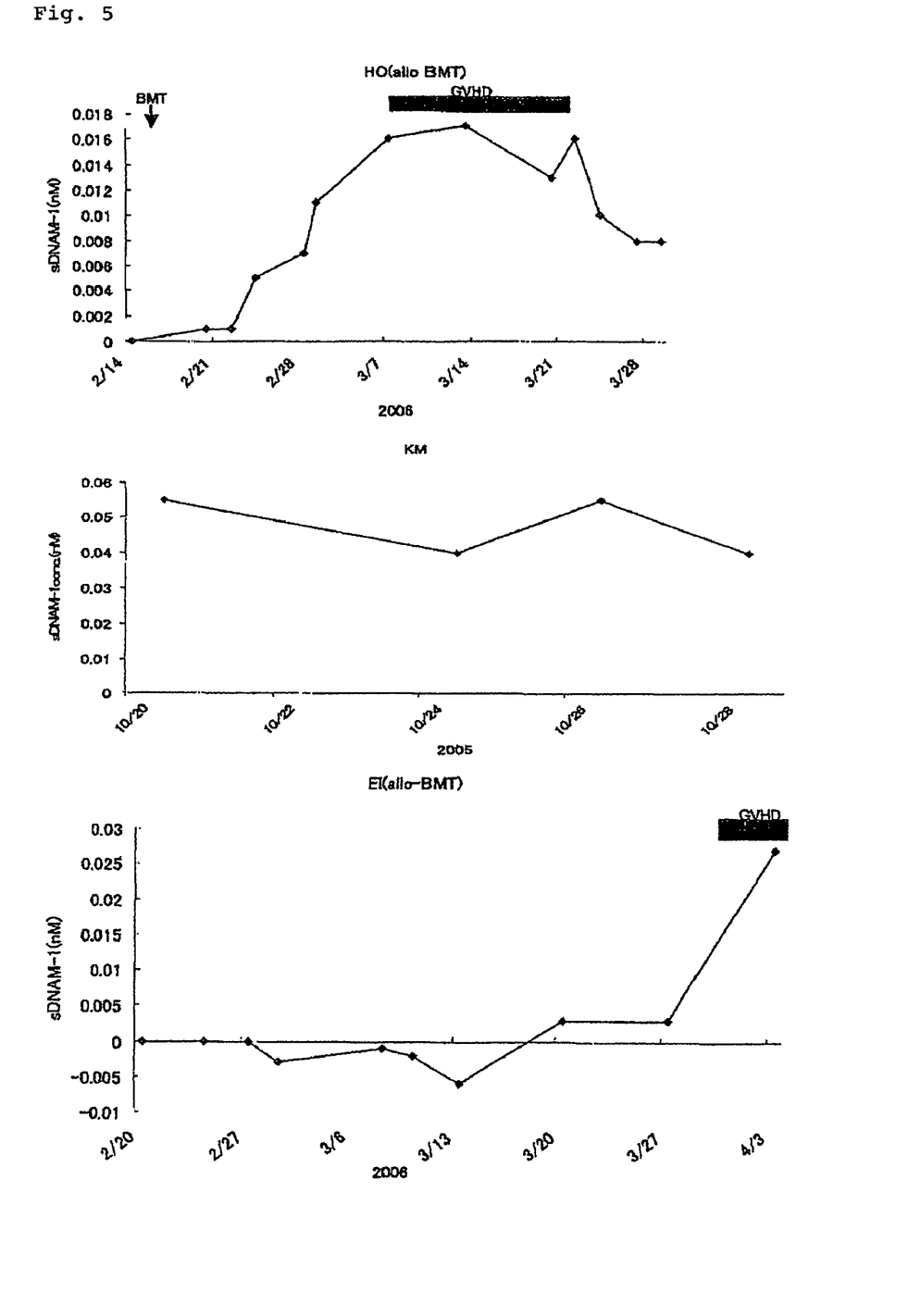
FIG. 5 indicates three patterns of temporal changes in blood DNAM-1 concentration based on test results with three subjects, wherein the negative values are as a result of data processing in the ELISA method (subtraction of the blank)

FIG. 5 indicates three patterns of temporal changes in blood DNAM-1 concentration based on test results with three patients. The graphs of patients YT and TO contain time points at least two of which have a higher DNAM-1 concentration than that of an immediately previous time point and which do not show a decreasing change. Contrastingly in the pattern of KM, there are no parts to be sectionalized in such manner.

Example 3

Changes in Blood DNAM-1 Concentration After Treatment of Acute GVHD Patients

Figure 61:
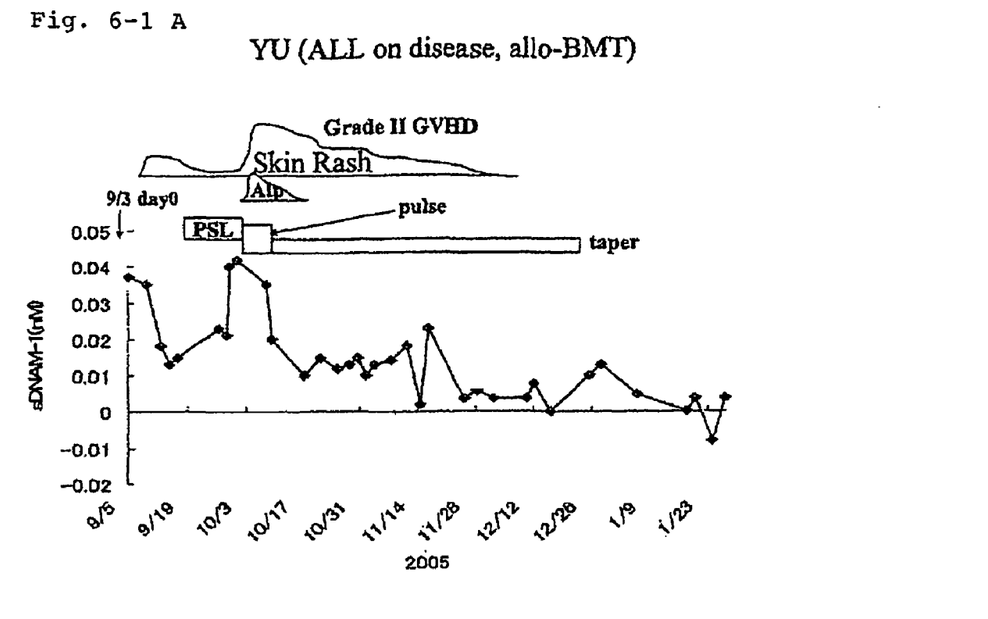
Figure 62:
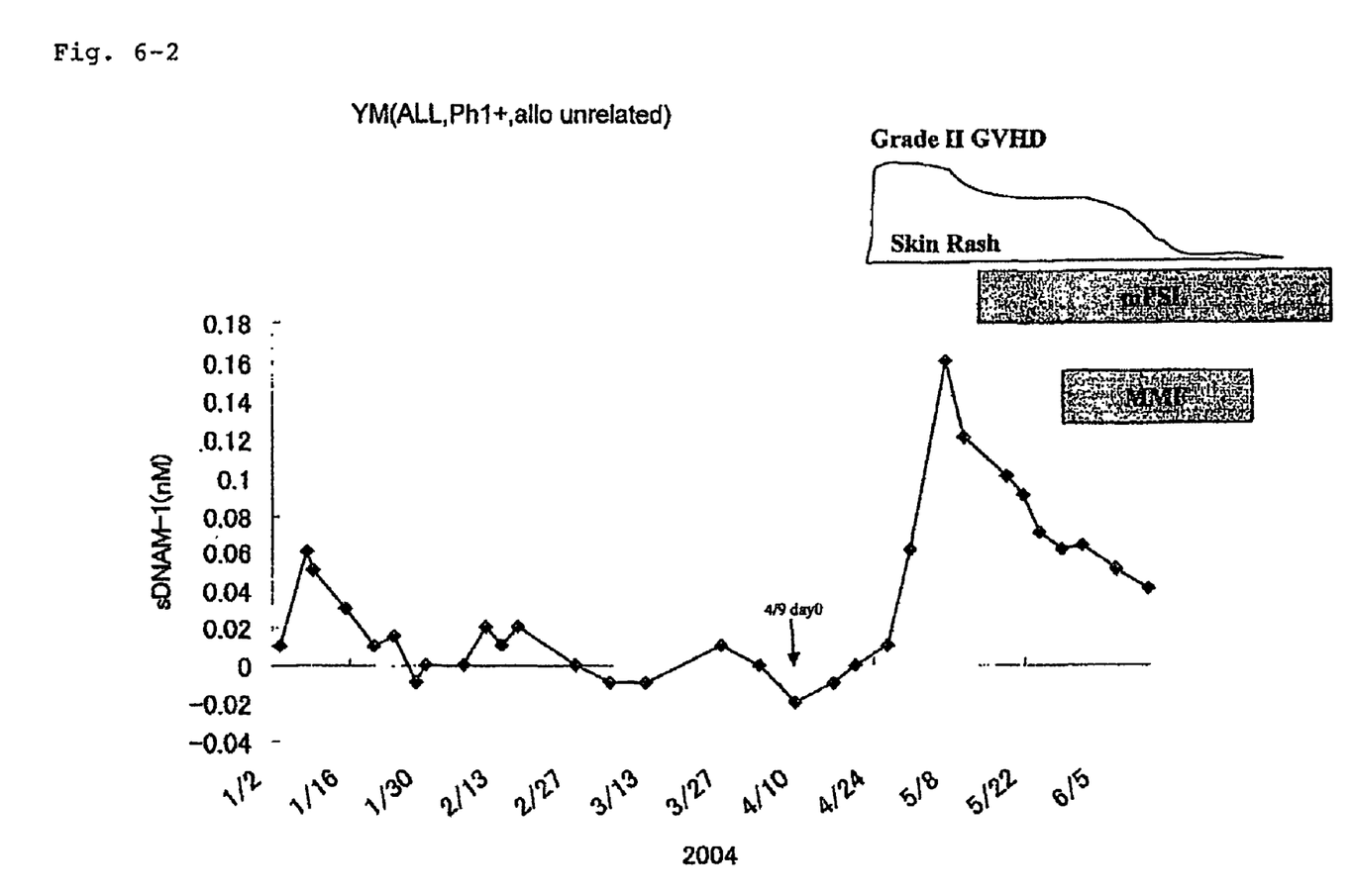

Temporal changes in blood DNAM-1 concentration after initiation of treatment were examined with respect to hematopoietic stem cell transplantation patients complicated with acute GVHD. The blood DNAM-1 concentration was followed starting from "Day 0" when acute GVHD was diagnosed and treatment was started. The blood DNAM concentration was measured by the ELISA method as described in Example 1. FIG. 6-1 follows temporal changes in blood DNAM-1 concentration of two acute GVHD patients. FIG. 6-2 shows a case in which the probability of acute GVHD occurrence could not be accurately predicted from changes in blood DNAM-1 concentration after hematopoietic stem cell transplantation and consequently the patient developed acute GVHD and was treated. Each figure also indicates observed symptoms. The results in the figures show that the blood DNAM-1 concentration after initiation of the treatment, and the transition thereof until remission are useful as monitoring markers indicating transition after treatment or as clinical data for determination of treatment effects.

The present invention enables detection of a slight sign leading to acute GVHD occurrence by means of classification of blood DNAM-1 concentrations and DNAM-1 indexes based on statistic analysis of data of temporal changes in DNAM-1 concentration. The invention is therefore extremely advantageous technology to plan a treatment or dose schedule appropriately for individual patients.

Example 4

DNAM-1 Molecular Targeted Therapy With Murine GVHD Models

DNAM-1 mouse homologous genes were cloned (Tahara-Hanaoka, et al., Biochem Biophys Res Column, 2005) and knockout mice were established (unpublished). A neutralizing antibody for the murine DNAM-1 was prepared (Tahara-Hanaoka, et al., Blood, 2006).

Figure 7:
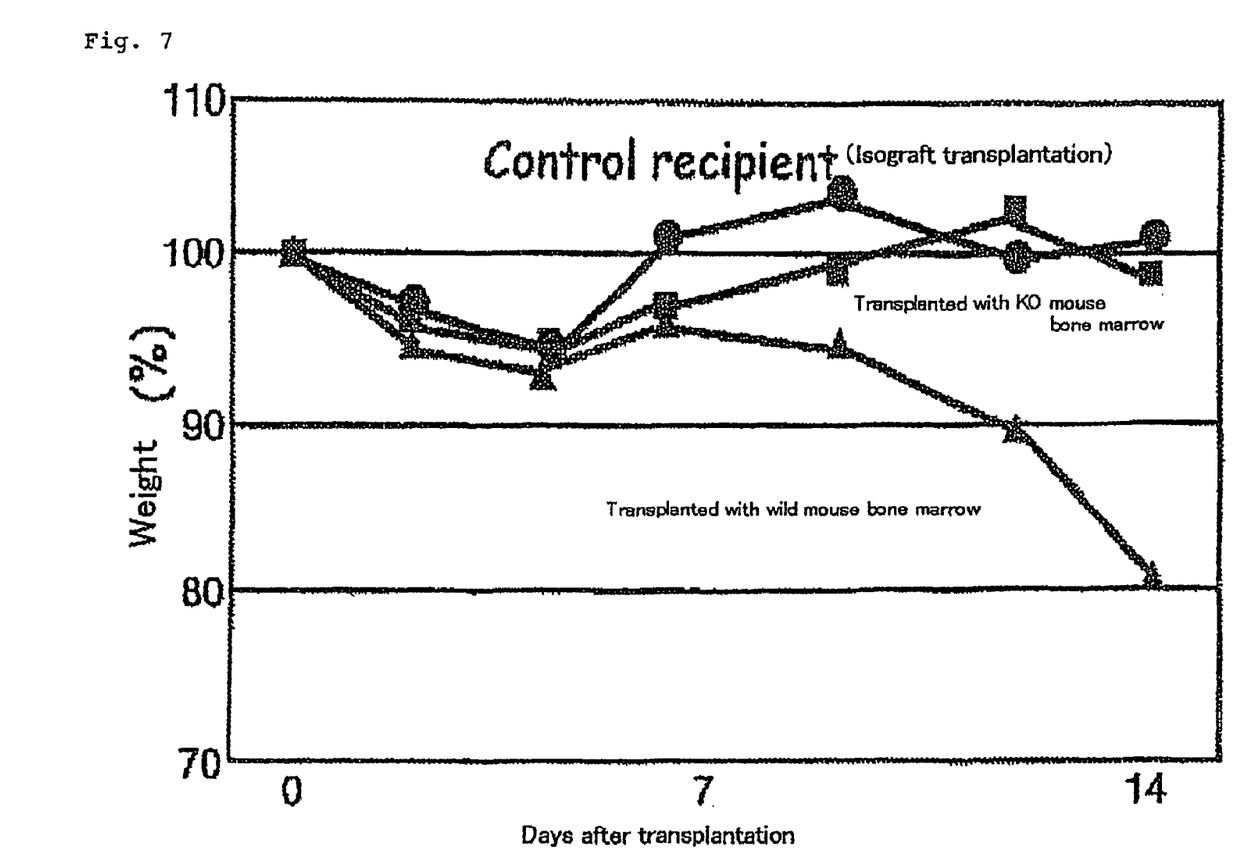
FIG. 7 is a graph showing involvement of DNAM-1 by experiment using GVHD models, wherein 1.0 Gy-irradiated C57BL6 mice were transplanted with bone marrow from BALB/C (wild type or KO type), "KO" means knockout.

To demonstrate the neutralizing activity of the antibody, acute GVHD models were prepared by transplanting C57BL/6 recipient mice (1.0 Gy-irradiated) with allogeneic bone marrow from BALB/C donor mice. Of the murine GVHD models, the C57BL/6 mice transplanted with bone marrow cells from DNAM-1 gene knockout mice (BALB/C background) were noticeably prevented from acute GVHD onset (FIG. 7).

Figure 8:
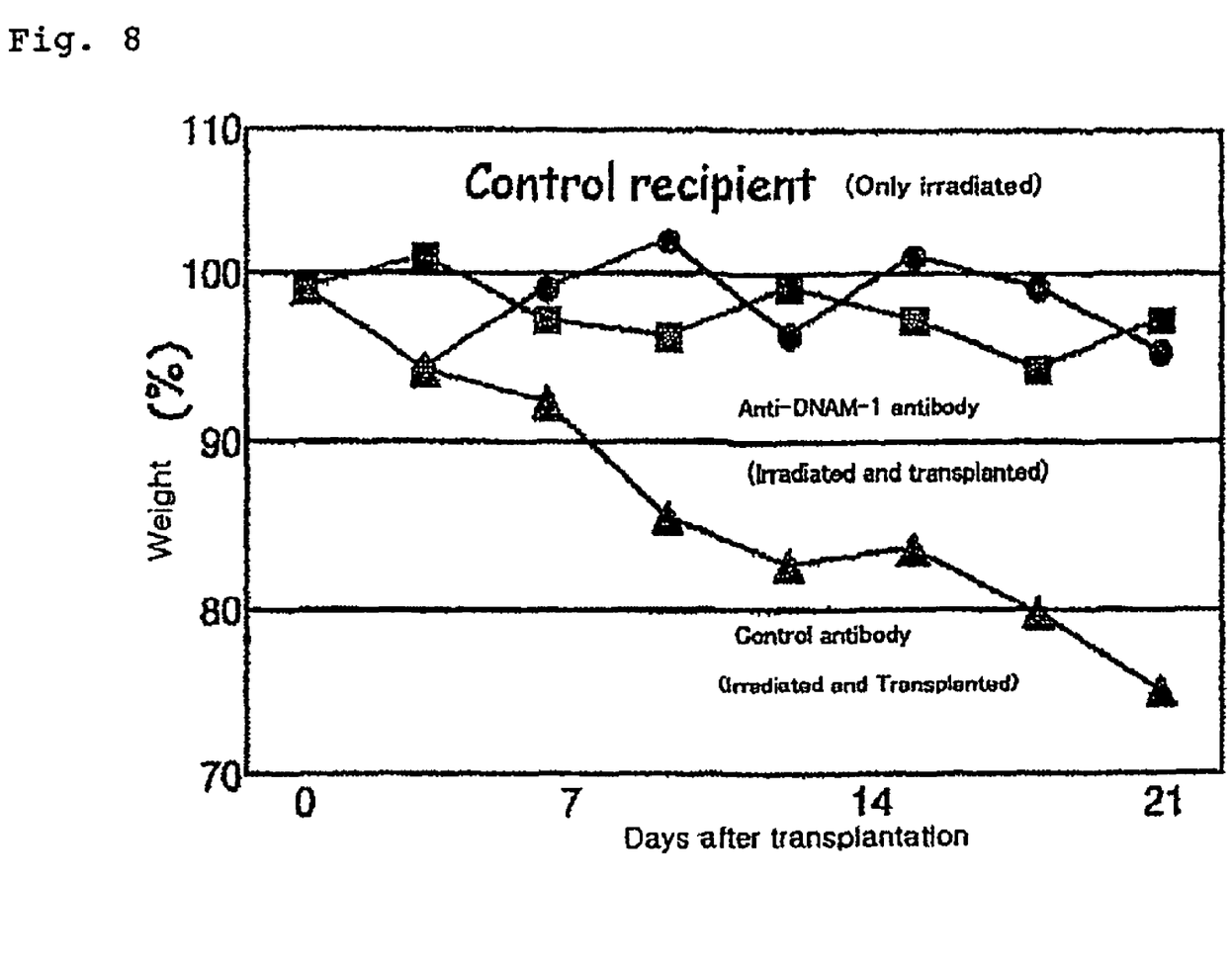
FIG. 8 is a graph indicating effects of anti-DNAM-1 antibody in GVHD models, wherein sublethally irradiated (0.4 Gy), BALB/C×C57BL/6 F1 mice were transplanted with spleen cells from BALB/C mice to prepare murine acute GVHD models, and wherein some recipient mice had been preliminarily administered with an anti-DNAM-1 neutralizing antibody (TX42).

Next, murine acute GVHD models were prepared by transplanting sublethally irradiated (0.4 Gy) BALB/C×C57BL/6 F1 mice with spleen cells from BALB/C mice. The recipient mice that had been preliminarily administered with the anti-DNAM-1 neutralizing antibody (TX42) were markedly prevented from acute GVHD onset (FIG. 8).

The above results strongly suggested that immunocytes involved in alloantigen specific immune response or inflammatory response related thereto were activated in acute GVHD to excrete soluble DNAM-1, and soluble or membrane DNAM-1 was in some way involved in acute GVHD. Further, acute GVHD was shown to be preventable or treatable by administering the anti-DNAM-1 antibody (TX42).

The invention claimed is:

1. A method of treating or reducing the risk of developing acute graft-versus-host disease (GVHD), comprising administering to a patient in need thereof a pharmaceutical preparation comprising a neutralizing anti-DNAM-1 antibody or an analogue thereof.

2. The method according to claim 1, wherein the anti-DNAM-1 antibody is a monoclonal antibody.

3. The method according to claim 1, wherein the anti-DNAM-1 antibody is a humanized DNAM-1 monoclonal antibody.

4. The method according to claim 1, wherein the pharmaceutical preparation further comprises at least a pharmaceutically acceptable excipient, carrier or stabilizing agent, or a medicinal substance as an effective component for acute GVHD treatment.

5. The method according to claim 2, wherein the pharmaceutical preparation further comprises at least a pharmaceutically acceptable excipient, carrier or stabilizing agent, and may further comprise a medicinal substance as an effective component for acute GVHD treatment.

6. The method according to claim 3, wherein the pharmaceutical preparation further comprises at least a pharmaceutically acceptable excipient, carrier or stabilizing agent, or a medicinal substance as an effective component for acute GVHD treatment.

* * * * *

UNITED STATES PATENT AND TRADEMARK OFFICE
Certificate

Patent No. 8,153,130 B2　　　　　　　　　　　　　　　　　　　　　Patented: April 10, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Akira Shibuya, Tsukuba (JP).

Signed and Sealed this Eleventh Day of November 2014.

*DANIEL KOLKER*
*Supervisory Patent Examiner*
Art Unit 1644
Technology Center 1600